United States Patent
Liu et al.

(10) Patent No.: US 10,464,881 B2
(45) Date of Patent: Nov. 5, 2019

(54) PROCESS FOR PREPARING Z-ENDOXIFEN OF HIGH PURITY

(71) Applicants: THE UNITED STATES OF AMERICA, AS REPRESENTED BY THE SECRETARY, DEPARTMENT OF HEALTH AND HUMAN SERVICES, Bethesda, MD (US); ALCHEM LABORATORIES CORPORATION, Alachua, FL (US)

(72) Inventors: Paul S. Liu, Bethesda, MD (US); Sergiy M. Denysenko, Alachua, FL (US); Guangfei Huang, Alachua, FL (US)

(73) Assignees: THE UNITED STATES OF AMERICA, AS REPRESENTED BY THE SECRETARY, DEPARTMENT OF HEALTH AND HUMAN SERVICES, Bethesda, MD (US); ALCHEM LABORATORIES CORPORATION, Alachua, FL (US)

( * ) Notice: Subject to any disclaimer, the term of this patent is extended or adjusted under 35 U.S.C. 154(b) by 0 days.

(21) Appl. No.: 15/770,274

(22) PCT Filed: Oct. 24, 2016

(86) PCT No.: PCT/US2016/058413
§ 371 (c)(1),
(2) Date: Apr. 23, 2018

(87) PCT Pub. No.: WO2017/070651
PCT Pub. Date: Apr. 27, 2017

(65) Prior Publication Data
US 2018/0305295 A1 Oct. 25, 2018

Related U.S. Application Data

(60) Provisional application No. 62/245,012, filed on Oct. 22, 2015.

(51) Int. Cl.
*C07C 213/10* (2006.01)
*C07C 41/30* (2006.01)
(Continued)

(52) U.S. Cl.
CPC .......... *C07C 213/10* (2013.01); *C07C 41/30* (2013.01); *C07C 45/455* (2013.01); *C07C 213/02* (2013.01); *C07B 2200/09* (2013.01)

(58) Field of Classification Search
CPC .................................................. C07C 213/10
See application file for complete search history.

(56) References Cited

FOREIGN PATENT DOCUMENTS

WO 2012050263 A1 4/2012

OTHER PUBLICATIONS

Rodríguez-Spong et al. Adv. Drug Delivery Rev. 56 (2004) 241-274.*
International Preliminary Report on Patentability dated Apr. 28, 2018; International Application No. PCT/US2016/058413; International Filing Date Oct. 24, 2016 (9 pages).
Ali et al.; "Endoxifen is a new potent inhibitor of PKC: A potential therapeutic agent for bipolar disorder"; Bioorganix & Medicinal Chemistry Letters 20 (2010); pp. 2665-2667.
Fauq et al.; "A convenient synthesis of (Z)-4-hydroxy-N-desmethyltamoxifen (endoxifen)", Biorganic & Medicinal Chemistry Letters 20 (2010) pp. 3036-3038.

(Continued)

Primary Examiner — Ana Z Muresan
(74) Attorney, Agent, or Firm — Cantor Colburn LLP

(57) ABSTRACT

Disclosed is a process for preparing (Z)-endoxifen, comprising (i) recrystallizing an input crystalline solid comprising a mixture of (Z)-endoxifen (1) and (E)-endoxifen (2) from a first solvent to provide a first crystalline solid and a first mother liquor, wherein the first mother liquor has a ratio of (1) to (2) at least 1.3 times greater than the ratio in the input crystalline solid (1) and (2); (ii) recrystallizing a solid produced by concentrating the first mother liquor, or by removal of the first solvent from the first mother liquor, from a second solvent to give a second crystalline solid and a second mother liquor; (iii) optionally recrystallizing the second crystalline solid from the second solvent one to five additional times to give a third crystalline solid; wherein the third crystalline solid has a ratio of (Z)-endoxifen (1) to (E)-endoxifen (2) greater than 20:1.

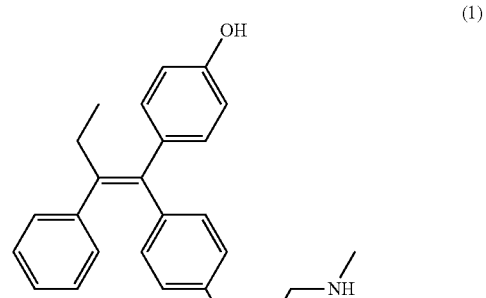

(1)

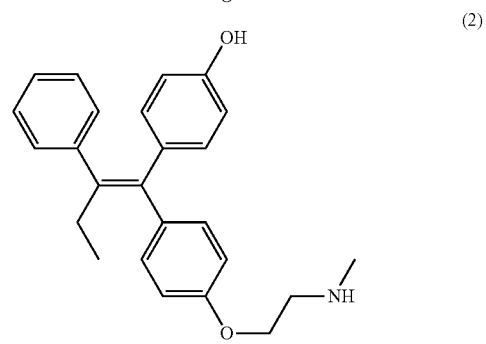

(2)

18 Claims, No Drawings

(51) Int. Cl.
    C07C 213/02    (2006.01)
    C07C 45/45     (2006.01)

(56) References Cited

OTHER PUBLICATIONS

International Search Report for International Application No. PCT/US2016-058413; International Filing Date Oct. 24, 2016; dated Feb. 8, 2017; 6 pages.
Lv et al.; "Design and Synthesis of Norendoxifen Analogues with Dual Aromatase Inhibitory and Estrogen Receptor Modulatory Activities"; Journal of Medicinal Chemistry; 2015; vol. 58; pp. 2623-2648.
Written Opinion of the International Search Report for International Application No. PCT/US2016-058413; International Filing Date Oct. 24, 2016; dated Feb. 8, 2017; 9 pages.
Yu, D., et al., "Simple and Efficient Production of (Z)-4-Hydroxytamoxifen, a Potent Estrogen Receptor Modulator" Journal of Organic Chemistry (2003) vol. 68, pp. 9489-9491.

* cited by examiner

PROCESS FOR PREPARING Z-ENDOXIFEN OF HIGH PURITY

CROSS-REFERENCE TO RELATED APPLICATIONS

This Application is a U.S. National Stage Application of PCT/US2016/058413 filed Oct. 24, 2016, which claims priority to U.S. Provisional Application No. 62/245,012 filed Oct. 22, 2015, each of which are incorporated by reference in their entirety.

STATEMENT OF GOVERNMENT SUPPORT

This invention was made with government support under HHSN261201200020C awarded by National Institutes of Health. The government has certain rights in the invention.

BACKGROUND

Some breast cancer cells require estrogen as a growth factor, the estrogen acting by binding to estrogen receptors on the cancer cells. Compounds which act as competitive estrogen receptor antagonists bind to the estrogen receptor without triggering the estrogen response, and can competitively block binding by native estrogen. Drugs which act through the competitive estrogen antagonism pathway have been successfully used to treat breast cancer.

Tamoxifen is an anticancer drug which has been used for over 40 years to reduce the risk of occurrence or recurrence of cancers, primarily breast cancer. Tamoxifen acts via estrogen receptor antagonism, but tamoxifen itself is actually a prodrug, and in its parent form has moderate to low affinity for the estrogen receptors in breast tissue. Tamoxifen's efficacy relies on metabolism in the liver by cytochrome P450 isoforms CYP2D6 and CYP3A4 to transform tamoxifen into the active metabolites, 4-hydroxytamoxifen (afimoxifene) and N-desmethyl-4-hydroxytamoxifen (endoxifen). Some patients do not respond to tamoxifen treatment because they do not produce adequate amounts of afimoxifen and endoxifen, sometimes due to low levels of the metabolizing enzymes. Giving the active (Z)-endoxifen form directly to tamoxifen non-responsive patients has been shown to result in significantly higher endoxifen blood levels compared to giving a similar dose of tamoxifen, and shows evidence of tumor regressions as shown in a phase I study.

Endoxifen exists as two forms, E and Z, with the Z form more active at the estrogen receptor. Endoxifen is frequently synthesized as a mixture of E and Z, with a difficult separation of isomers required to obtain pure Z isomer. Some procedures in the art separate the E and Z isomers via methods which are expensive and difficult to perform on larger scale, such as preparative HPLC. Thus there is a need in the art for a practical, scalable synthesis that gives access to highly pure (Z)-endoxifen.

SUMMARY

This disclosure is directed to a new process for the preparation of the active metabolite of tamoxifen, (Z)-endoxifen. The procedure provides a very attractive approach for obtaining the compound as it proceeds efficiently from commercially available starting materials and without the need of protection and de-protection steps. It also avoids the use of chromatography in the separation of the Z- and E-isomers and enables facile scale-up operations in multi-kilogram quantities. The conversion of the E-isomer by-product to additional Z-isomer is accomplished via an innovative recycling procedure, which uses thermal isomerization exclusively, and selective recrystallizations with two different solvents. A first solvent, which can be isopropyl acetate, serves the dual functions as the equilibration medium and solvent with the suitable differential solubility between the E- and Z-isomers. Recrystallization of the isomeric mixture in the first solvent results in the preferential removal of the E-isomer as a solid and enrichment of the Z-isomer in the supernatant. Recrystallization of similar mixtures in the second solvent, which can be acetone, allows the precipitation of Z-isomer with increasing isomeric purity. The combined methodology greatly enhances the efficiency and productivity of the new process.

The present disclosure provides a process for the synthesis of (Z)-endoxifen by (i) recrystallizing an input crystalline solid comprising a mixture of (Z)-endoxifen (1) and (E)-endoxifen (2) from a first solvent to provide a first crystalline solid and a first mother liquor, wherein the first mother liquor has a ratio of (1) to (2) at least 1.3 times greater than the ratio in the input crystalline solid;

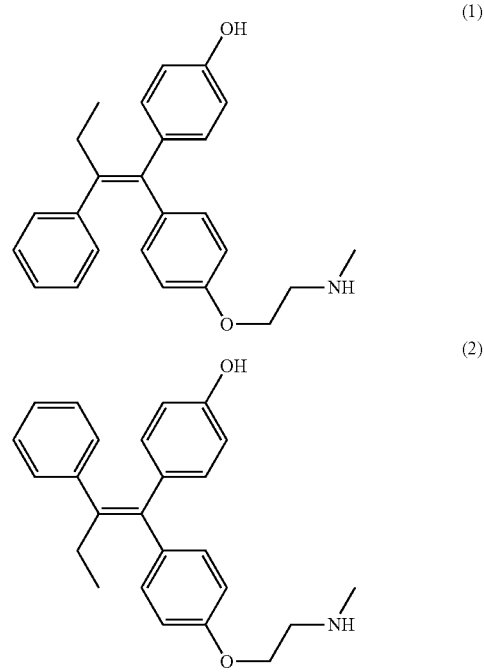

(ii) recrystallizing a solid produced by concentrating the first mother liquor or by removal of the first solvent from the first mother liquor, from a second solvent to give a second crystalline solid and a second mother liquor;

(iii) optionally recrystallizing the second crystalline solid from the second solvent one to five additional times to give a third crystalline solid;

wherein the third crystalline solid has a ratio of (Z)-endoxifen (1) to (E)-endoxifen (2) greater than 20:1.

The disclosure also includes a process for preparing (Z)-endoxifen, comprising (i) dissolving a mixture of (Z)-endoxifen (1) and (E)-endoxifen (2) in isopropyl acetate, wherein the mixture contains has a ratio of (1) to (2) that is less than 1:1;

(ii) heating the mixture of (1) and (2) in isopropyl acetate at a temperature of 55° C. to 88° C. to obtain a second mixture of (1) and (2) having a ratio of (1) to (2) of about 1:1; and (iii) cooling the mixture to form a crystalline solid and a first mother liquor;

(iv) removing the first mother liquor from the crystalline solid; and (v) evaporating the first mother liquor to form a solid having a ratio of (1) to (2) that is greater than 1:1; or greater than 1.3:1, or greater than 1.5:1. The crystalline solid formed in step (iii) contains more (E)-endoxifen (2) than (Z)-endoxifen (1). In some embodiments the crystalline solid formed in step (iii) is subjected to steps (i) to (iii) one or more additional times to produce more (Z)-endoxifen.

DETAILED DESCRIPTION

Terminology

Compounds are described using standard nomenclature. Unless defined otherwise, all technical and scientific terms used herein have the same meaning as is commonly understood by one of skill in the art to which this invention belongs.

The terms "a" and "an" do not denote a limitation of quantity, but rather denote the presence of at least one of the referenced items. The term "or" means "and/or". The terms "comprising," "having," "including," and "containing" are to be construed as open-ended terms (i.e., meaning "including, but not limited to").

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art of this disclosure.

Furthermore, the disclosure encompasses all variations, combinations, and permutations in which one or more limitations, elements, clauses, and descriptive terms from one or more of the listed claims are introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group.

All compounds are understood to include all possible isotopes of atoms occurring in the compounds. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$.

The opened ended term "comprising" includes the intermediate and closed terms "consisting essentially of" and "consisting of."

"Halo" or "halogen" means fluoro, chloro, bromo, or iodo.

A significant change is any detectable change that is statistically significant in a standard parametric test of statistical significance such as Student's T-test, where $p<0.05$.

Chemical Description

The disclosure includes the following embodiments, which should not be construed as limiting. Rather, these embodiments are exemplary and are provided to describe the invention to those skilled in the art. Like reference numerals refer to like elements throughout.

It has been unexpectedly discovered that isopropyl acetate (iPrOAc) can equilibrate a mixture of (Z)-endoxifen (1) and (E)-endoxifen (2) containing less than 50% Z-endoxifen to a 1:1 mixture of (Z)-endoxifen (1) and (E)-endoxifen (2) by heating. After heating, crystallization can be used to remove a crystalline solid containing primarily the unwanted E-isomer, and provide a mother liquor containing a mixture of (Z)- and (E)-endoxifen, but which is predominantly (Z)-endoxifen, for example the mother liquor may contain about 70% (Z)-endoxifen. This process is distinct from the usual crystallization procedure, which provides a crystalline solid containing mainly the desired (Z)-isomer.

In an embodiment the disclosure includes a process for the synthesis of (Z)-endoxifen by:

(i) recrystallizing an input crystalline solid comprising a mixture of (Z)-endoxifen (1) and (E)-endoxifen (2) from a first solvent to provide a first crystalline solid and a first mother liquor, wherein the first mother liquor has a ratio of (1) to (2) at least 1.3 times greater than the ratio in the input crystalline solid;

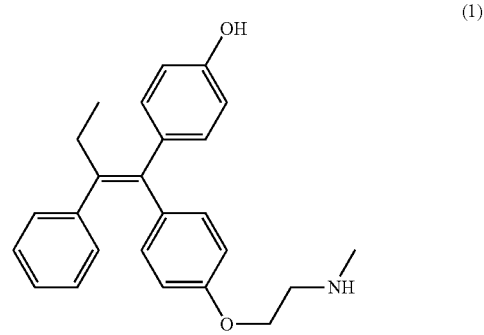

(1)

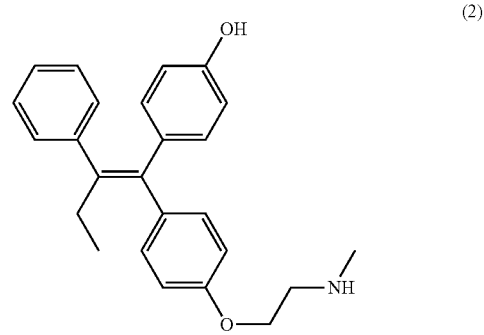

(2)

(ii) recrystallizing a solid produced by concentrating the first mother liquor, or by removal of the first solvent from the first mother liquor, from a second solvent to give a second crystalline solid and a second mother liquor;

(iii) optionally recrystallizing the second crystalline solid from the second solvent one to five additional times to give a third crystalline solid;

wherein the third crystalline solid has a ratio of (Z)-endoxifen (1) to (E)-endoxifen (2) greater than 20:1.

The initial step (i) in the disclosed process is the recrystallizing of an input crystalline solid comprising a mixture of (Z)-endoxifen (1) and (E)-endoxifen (2) from a first solvent to provide a first crystalline solid and a first mother liquor, wherein the first mother liquor has a ratio of (1) to (2) at least 1.3 times greater than the ratio in the input crystalline solid;

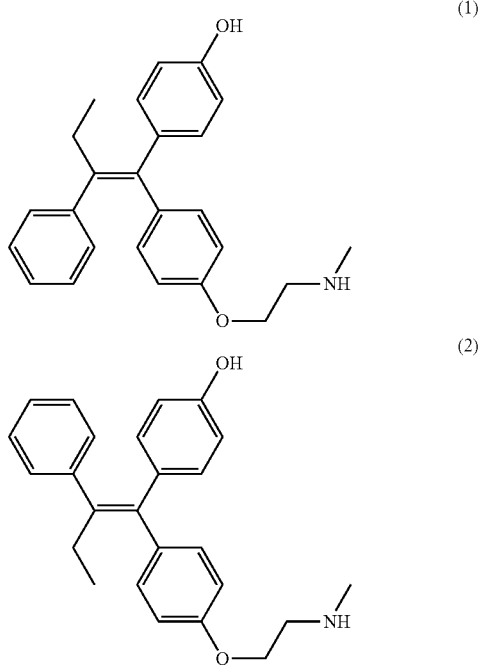

Generally, this recrystallizing can be carried out in a first solvent in which the E isomer (2) crystallizes well and is significantly less soluble than the Z isomer (1). It has been unexpectedly discovered that toluene, isopropyl acetate, methyl ethyl ketone, and methyl isobutyl ketone are particularly useful first solvents for carrying out this step, with isopropyl acetate particularly preferred. The recrystallization can be performed by dissolving the input crystalline solid in the first solvent at a first temperature of 40 to 100° C. and then cooling the solution by 20 to 100° C. to a second temperature to effect crystallization. The solution can be held at the second temperature for several hours to allow for adequate crystallization. For example, the input crystalline solid can be dissolved in isopropyl acetate at 70 to 100° C. or 80 to 90° C., and then the resulting solution is cooled to 0 to 40° C. or 20 to 30° C., and held at the second temperature for 0.5 hours to 10 days, preferably 2 to 24 hours. In some cases longer holding times at the second temperature may be required. The first crystalline solid and the first mother liquor may be separated by filtration, decanting, aspiration, or any suitable method. The separated first crystalline solid may be washed with a suitable solvent to remove impurities, and can be dried with or without heat and/or reduced pressure to remove solvent. Preferably, the first crystalline solid is collected by filtration, washed with first solvent, and dried in vacuo to constant weight. The separated mother liquor can be concentrated in vacuo to give a solid or a non-solid, and can be can be dried with or without heat and/or reduced pressure to remove solvent. Preferably, the concentrated mother liquor is dried in vacuo to constant weight.

The measurement of ratios of (1) to (2) can be accomplished by HPLC as given in the general methods section, as well as by other methods.

The ratio of (1) to (2) in the first mother liquor can be from 1.3 to 100 times greater, or more than 1.3, 1.5, 2, 5, 10 or 20 times greater than the ratio of (1) to (2) in the input crystalline solid. The ratio of (1) to (2) in the first mother liquor can be from 2 to 40, or from 3 to 10, or from 4 to 5 times greater than the ratio of (1) to (2) in the input crystalline solid.

The ratio of (1) to (2) in the first crystalline solid can be from 1.3 to 100 times lower, or more than 1.3, 1.5, 2, 5, 10 or 20 times lower than the ratio of (1) to (2) in the input crystalline solid. The ratio of (1) to (2) in the first crystalline solid can be from 1.3 to 40, or from 2 to 10, or from 2 to 4 times lower than the ratio of (1) to (2) in the input crystalline solid.

The second step (ii) in the disclosed process is recrystallizing a solid produced by concentrating the first mother liquor, or by removal of the first solvent from the first mother liquor, from a second solvent to give a second crystalline solid and a second mother liquor.

Generally, this recrystallizing can be carried out in a second solvent in which the Z isomer (1) crystallizes well and in which enrichment of the Z isomer can be increased upon crystallization. It has been unexpectedly discovered that acetone is a particularly useful second solvent for carrying out this step. Other solvents, such as methanol, ethanol, or methyl acetate, may also be used as the second solvent. The recrystallization can be performed by dissolving the input crystalline solid in the second solvent at a first temperature of 20 to 100° C. and then cooling the solution by 20 to 100° C. to a second temperature to effect crystallization. The solution can be held at the second temperature for several hours to allow for adequate crystallization. For example, a solid formed from the concentrated first mother liquor can be dissolved in acetone from 20 to 47° C. (reflux temperature of acetone), preferably from 40 to 47° C., and then the resulting solution is cooled to −10 to 20° C. or 0 to 10° C., and held at the second temperature for 0.5 hours to 10 days or 2 to 72 hours. In some cases longer holding times at the second temperature may be required. The second crystalline solid and the second mother liquor may be separated by filtration, decanting, aspiration, or any suitable method. The separated second crystalline solid may be washed with a suitable solvent to remove impurities, and can be dried with or without heat and/or reduced pressure to remove solvent. The separated mother liquor can be concentrated in vacuo to give a solid, and can be can be dried with or without heat and/or reduced pressure to remove solvent. Preferably, the second mother liquor is separated from the second crystalline solid by aspiration, concentrated and dried in vacuo to constant weight.

The ratio of (1) to (2) in the second crystalline solid can be from 1.2 to 200, or 1.3 to 100, or 1.5 to 50, or 1.3 to 10 times higher than the ratio of (1) to (2) in the first mother liquor. The ratio of (1) to (2) in the second crystalline solid can be from 1.3 to 40, or 2 to 10, or from 2 to 4 times higher than the ratio of (1) to (2) in the input crystalline solid.

The third step (iii) is optionally recrystallizing the second crystalline solid from the second solvent one or more additional times to give a third crystalline solid, wherein the third crystalline solid has a ratio of (Z)-endoxifen (1) to (E)-endoxifen (2) greater than 20:1. This ratio may also be at least 1.3 times greater than the ration of (Z)-endoxifen (1) to (E)-endoxifen (2) in the second crystalline solid.

The ratio of (1) to (2) in the second crystalline solid can be greater than 20:1, or greater than 50:1. The ratio of (1) to (2) in the third crystalline solid can be greater than 20:1, or greater than 50:1, or greater than 100:1.

In some embodiments the process includes generating the input crystalline solid by reacting 4-(1-(4-(2-haloethoxy)phenyl)-2-phenylbut-1-enyl)phenol (3) with methylamine to produce a mixture of (Z)-endoxifen (1) and (E)-endoxifen (2), wherein X is chloro, bromo, or iodo

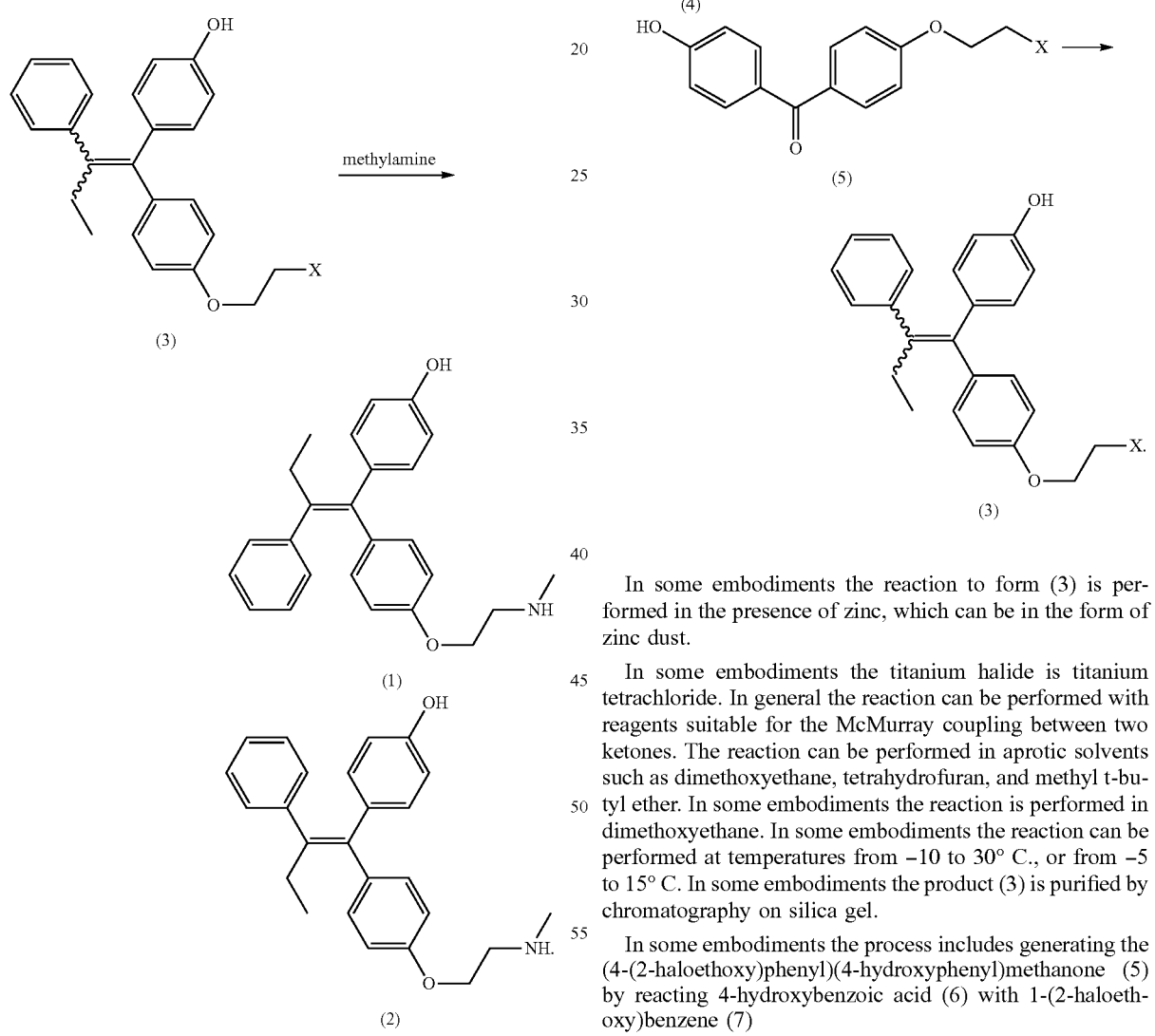

In some embodiments the reaction of (3) with methylamine occurs in hydroxylic solvent, such as ethanol, methanol, or isopropanol. In some embodiments the reaction of (3) with methylamine occurs in methanol solvent. In some embodiments the reaction of (30 with methylamine occurs at a temperature from 30 to 50° C. When complete, the reaction of (3) can be concentrated, taken up in organic solvent, and washed with mild aqueous base such as $NaHCO_3$ or $Na_2CO_3$, and concentrated to give a solid. The product mixture of (1) and (2) can be recrystallized from a solvent such as acetone.

In some embodiments the process includes generating the 4-(1-(4-(2-haloethoxy)phenyl)-2-phenylbut-1-enyl)phenol (3) by reacting propiophenone (4) with (4-(2-haloethoxy)phenyl)(4-hydroxyphenyl)methanone (5) in the presence of a titanium halide reagent

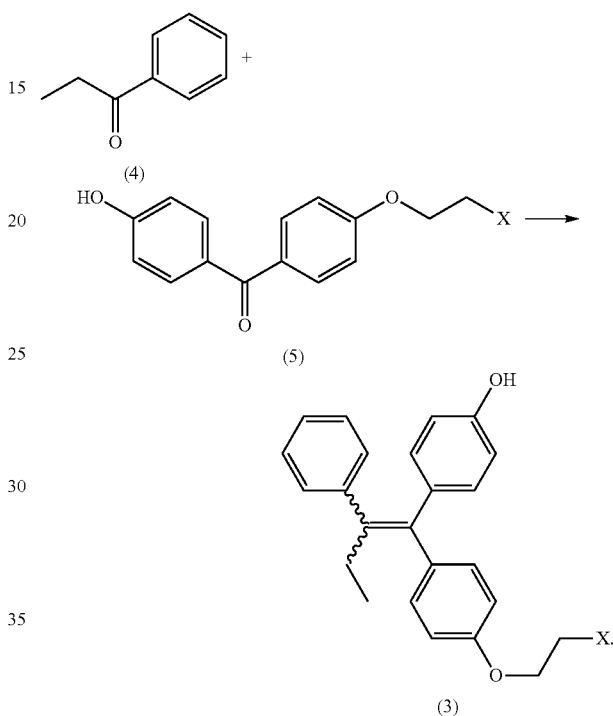

In some embodiments the reaction to form (3) is performed in the presence of zinc, which can be in the form of zinc dust.

In some embodiments the titanium halide is titanium tetrachloride. In general the reaction can be performed with reagents suitable for the McMurray coupling between two ketones. The reaction can be performed in aprotic solvents such as dimethoxyethane, tetrahydrofuran, and methyl t-butyl ether. In some embodiments the reaction is performed in dimethoxyethane. In some embodiments the reaction can be performed at temperatures from −10 to 30° C., or from −5 to 15° C. In some embodiments the product (3) is purified by chromatography on silica gel.

In some embodiments the process includes generating the (4-(2-haloethoxy)phenyl)(4-hydroxyphenyl)methanone (5) by reacting 4-hydroxybenzoic acid (6) with 1-(2-haloethoxy)benzene (7)

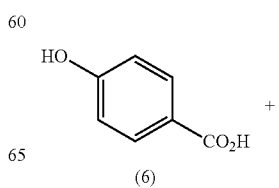

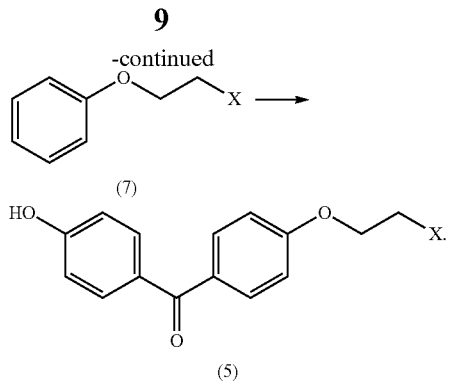

(7)

(5)

In some embodiments the reaction to form (5) is performed in the presence of Bronsted or Lewis acid. The acid can be metal halide Lewis acids such as zinc bromide, iron trichloride, or aluminum trichloride. Other acids such as polyphosphoric acid, or phosphorus trihalides can be used. In some embodiments the reaction to form (5) is performed in the presence of zinc bromide, phosphorus tribromide and polyphosphoric acid. When complete, the reaction product mixture containing (5) can be concentrated, taken up in organic solvent, washed with aqueous base, and concentrated.

The X group can be any leaving group which is stable enough to survive until the reaction of compound (3), but can be displaced by methylamine in the reaction of compound (3). X can be halogen (such as chloro, bromo, or iodo), sulfonate (such as methane sulfonate or p-toluenesulfonate), or other suitable leaving groups. Preferably X is halogen, more preferably X is bromo.

In some embodiments X is bromo.

In some embodiments the first solvent is isopropyl acetate, toluene, methyl ethyl ketone, or methyl isobutyl ketone.

In some embodiments the first solvent is isopropyl acetate.

In some embodiments the second solvent is acetone. In some embodiments the second solvent is methanol, ethanol, or acetone.

In some embodiments the third crystalline solid has a ratio of (Z)-endoxifen (1) to (E)-endoxifen (2) of 50:1 or greater.

In some embodiments each recrystallization requires dissolving the compound or compounds to be recrystallized in solvent that is at a first temperature, and then cooling the resulting solution to a second temperature 20 to 100° C. lower than the first temperature. The first and second temperatures are selected based on the nature of the solvent. The cooling can be rapid or gradual, and can take from 1 minute to 24 hours or more.

In some embodiments, "recrystallizing" can be crystallizing from a nonsolid or semi-solid form, such as a syrup that has been concentrated but not solidified.

In some embodiments the recrystallizing of the second crystalline solid in step (ii) is performed 2 times to obtain the third crystalline solid.

In some embodiments the process includes a fourth step (iv) isomerizing a crystalline solid or mother liquor formed according to previous embodiments wherein the ratio of (Z)-endoxifen (1) to (E)-endoxifen (2) is less than 0.9 to 1, by dissolving the crystalline solid or mother liquor in a third solvent and heating at a temperature from 60 to 100° C. for 0.5 to 4 hours, to produce an isomerized solution with a ratio of (Z)-endoxifen (1) to (E)-endoxifen (2) of approximately 1:1.

The isomerizing can be performed at temperatures from 40 to 150° C., depending on the solvent. In some embodiments the isomerizing is performed at a temperature from 60 to 100° C., or from 70 to 90° C. Preferably the isomerizing is performed in isopropyl acetate at a temperature from 70 to 90° C.

In some embodiments the isomerizing can be performed in the presence of acid. The acid can be a weak acid such as acetic acid, propionic acid, or citric acid, or the acid can be a strong acid such as hydrochloric, p-toluenesulfonic, or trifluoroacetic acid.

In some embodiments the process further comprises concentrating the isomerized solution to form an isomerized crystalline solid, and using the isomerized crystalline solid as the input crystalline solid for steps (i) through (iii).

In some embodiments the process further includes a fifth step, (v) cooling the isomerized solution by 30 to 100° C. to form a fourth crystalline solid and a fourth mother liquor, and removing the mother liquor followed by resubjecting the fourth crystalline solid to step (iv) followed by cooling and crystallization at least two times or three or more times, and combining the resulting mother liquors to provide a combined mother liquor with a ratio of (Z)-endoxifen (1) to (E)-endoxifen (2) of at least 1.5 to 1.

In some embodiments the fourth mother liquor is removed by aspiration, concentrated in vacuo and dried to solid weight.

In some embodiments the combined mother liquor is concentrated in vacuo and dried to solid weight.

In some embodiments the process further comprises designating the combined mother liquor as a first mother liquor and subjecting it to the same steps that would be used for a first mother liquor. In this way isomerized material can be used to produce more Z-endoxifen product.

In some embodiments the third solvent is isopropyl acetate.

In some embodiments the third solvent is the same as the first solvent. In some embodiments both the first solvent and third solvent are isopropyl acetate.

In an embodiment, the disclosure includes a process for preparing (Z)-endoxifen, including a first step (i) of recrystallizing an input crystalline solid comprising a mixture of (Z)-endoxifen (1) and (E)-endoxifen (2) from isopropyl acetate to provide a first crystalline solid and a first mother liquor, wherein the first mother liquor has a ratio of (1) to (2) at least 1.3 times greater than the ratio in the input crystalline solid;

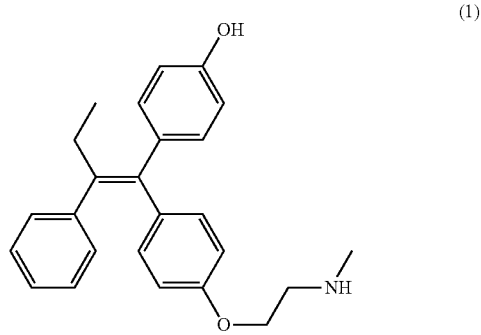

(1)

11
-continued

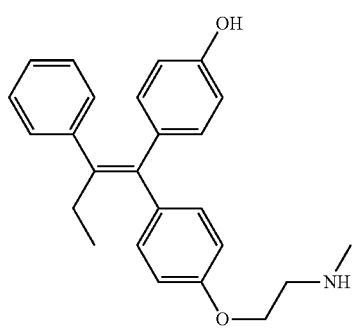

(2)

A second step (ii) of concentrating the first mother liquor, then crystallizing the concentrated first mother liquor from acetone to give a second crystalline solid and a second mother liquor; and A third step (iii) of optionally recrystallizing the second crystalline solid from acetone one to five additional times to give a third crystalline solid;

wherein the third crystalline solid has a ratio of (Z)-endoxifen (1) to (E)-endoxifen (2) greater than 20:1.

In an embodiment, the disclosure includes a process for preparing a mixture of (Z)-endoxifen (1) and (E)-endoxifen (2), including reacting 4-(1-(4-(2-bromoethoxy)phenyl)-2-phenylbut-1-enyl)phenol (3) with methylamine to produce a mixture of (Z)-endoxifen (1) and (E)-endoxifen (2).

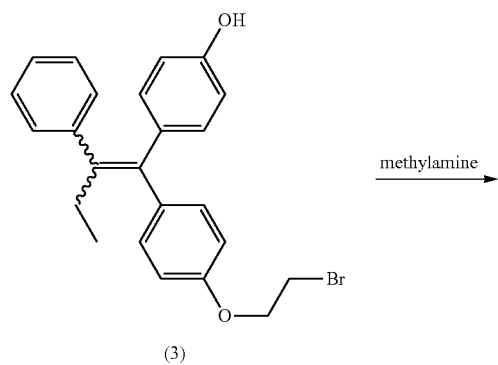

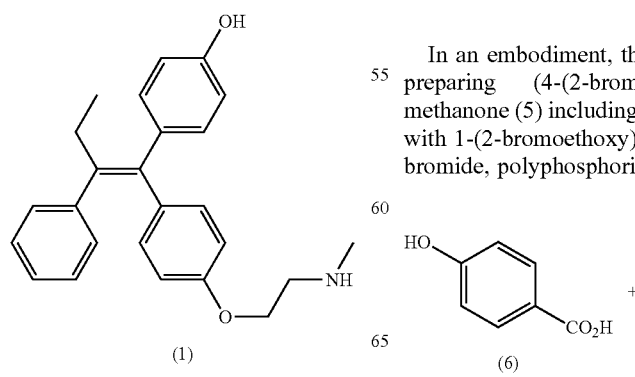

12
-continued

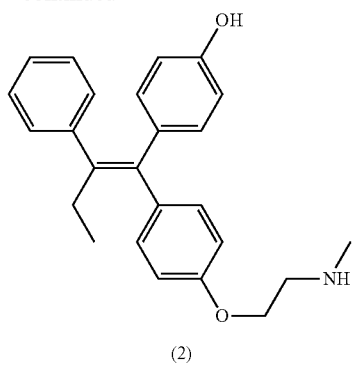

(2)

In an embodiment, the disclosure includes a process for preparing 4-(1-(4-(2-bromoethoxy)phenyl)-2-phenylbut-1-enyl)phenol (3) including reacting propiophenone (4) with (4-(2-bromoethoxy)phenyl)(4-hydroxyphenyl)methanone (5) in the presence of zinc and titanium tetrachloride.

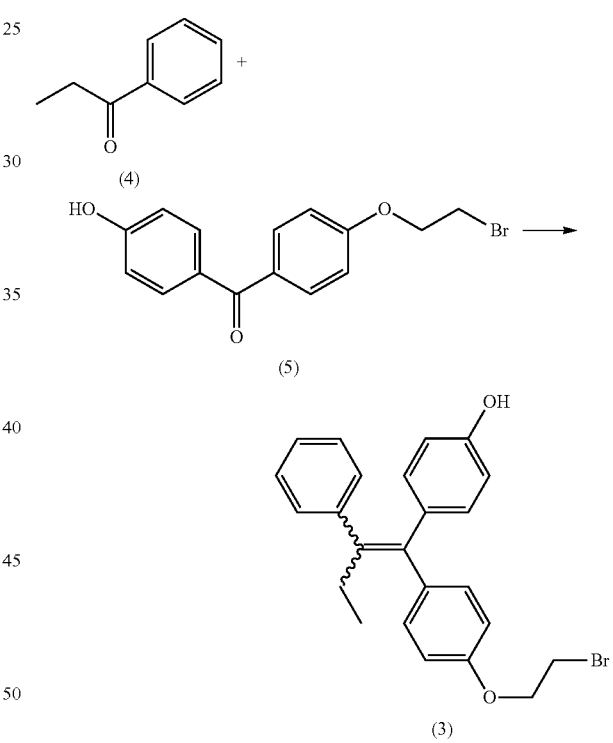

In an embodiment, the disclosure includes a process for preparing (4-(2-bromoethoxy)phenyl)(4-hydroxyphenyl) methanone (5) including reacting 4-hydroxybenzoic acid (6) with 1-(2-bromoethoxy)benzene (7) in the presence of zinc bromide, polyphosphoric acid, and phosphorus tribromide.

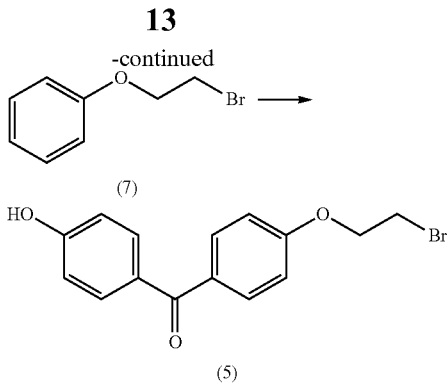

EXAMPLES

Abbreviations

HPLC High Performance Liquid Chromatography
iPrOAc Isopropyl Acetate
MEK Methyl Ethyl Ketone
MiBK Methyl Isobutyl Ketone
NMR Nuclear Magnetic Resonance
TLC Thin Layer Chromatography

General Methods

The reagents and solvents used were commercial anhydrous grade. They were used without further purification. Column chromatography was carried out over silica gel (100-200 mesh). $^1$H- and $^{13}$C NMR spectra were recorded on a 300 MHz spectrometer from solutions in CDCl$_3$, methanol-d4, and DMSO-d6. HPLC was performed using a Waters separation module with a Waters 2487 Dual absorbance detector or a Shimadzu system LC-2010CHT with diode array detection. The chromatography conditions included a Phenomenex Luna Phenyl-Hexyl column (4.6× 150 mm, 5 m), elution with a flow rate of 1.0 mL/min, and a gradient of mobile phase A:mobile phase B from 100:0 to 0:100. Mobile phase A was 40:60 10 mM ammonium formate in water, pH 4.3:10 mM ammonium formate in methanol, and mobile phase B was 10 mM ammonium formate in methanol.

Example 1. Crystallization of 1:1 Mixtures of Z and E Endoxifen

A given weight of a 1:1 mixture of (Z) Endoxifen (1) and (E) endoxifen (2) was dissolved in a given amount of solvent at a temperature between 45 and 80° C. (in any case no higher than the boiling point of the solvent) and was then kept at a given crystallization temperature for 16 hours (except for entry 10 where crystallization was stopped at 4 hours), at which point the mixture was filtered to recover a solid and a filtrate. The ratio of Z/E endoxifen in solid and filtrate was measured by HPLC. The results are shown in table 1. The goal was to have high Z/E ratio in either solid or filtrate, and the results show that only the filtrates (mother liquors) had ratios greater than 1/1. Acetone solvent sometimes gave good results but was very inconsistent. The best results came from solvents toluene, isopropyl acetate (iPrOAc), methyl ethyl ketone (MEK), and methyl isobutyl ketone (MiBK), each of which had Z/E ratios of 70/30 or greater in the filtrate. Isopropyl acetate was chosen as the solvent for further experiments based on its lower toxicity.

TABLE 1

Results of Crystallization of Endoxifen Z/E 1:1 mixtures

| Entry | Solvent | Sample Amount | Solvent Amount | Crystal Temp | Solid Yield | Z/E Solid | Z/E Filtrate |
|---|---|---|---|---|---|---|---|
| 1 | Acetone | 4.1 g | 27 ml | 21° C. | 3.2 g (80%) | 42/57 | 60/25 |
| 2 | Acetone | 3.2 g | 32 ml | 21° C. undisturbed | 1.26 g (39%) | 1.6/97.6 | 71/24 |
| 3 | Acetone | 1 g | 6 ml | 0° C. | 700 mg (70%) | 43/56 | 37/40 |
| 4 | Acetone | 9.3 g | 55 ml | 21° C. | 2.99 g (32%) | 25/74 | 55/16 |
| 5 | Acetone | 7.5 g | 63 ml | 0° C. | 5.35 g (71%) | 38/61 | 52/41 |
| 6 | Acetone | 7.5 g | 90 ml | 0° C. | 4.8 g (64%) | 38/62 | 52/40 |
| 7 | MEK | 1 g | 6 ml | 0° C., then 10° C. | 392 mg (39%) | 9/91 | 74/20 |
| 8 | MEK | 1 g | 3.5 ml | 16° C. | 366 mg (36%) | 5/95 | 75/16 |
| 9 | iPrOAc | 1 g | 6 ml | 16° C. | 365 mg (36%) | 6/93 | 78/16 |
| 10 | iPrOAc | 7.3 g | 45 ml | 21° C., 4h | 1.8 g (25%) | 8/91 | 70/28 |
| 11 | iPrOAc | 15 g | 130 ml | 21° C. | 6.2 g (36%) | 2.7/96.3 | 78/18 |
| 12 | Toluene | 70 mg | 0.4 ml | 20° C. | 25 mg (36%) | 8/92 | 78/22 |
| 13 | Anisole | 0.9 g | 20 ml | 0° C. | 220 mg (24%) | 4.3/93 | 65/34 |
| 14 | MiBK | 1 g | 6 ml | 0° C. | 340 mg (34%) | 5/94 | 74/18 |

Example 2. Synthesis of (4-(2-bromoethoxy)phenyl)(4-hydroxyphenyl)methanone (5)

Zinc bromide (3.011 kg, 13.1 mol) and polyphosphoric acid (16.5 kg) were charged into a 20-L reaction vessel and stirred well while heated to 45° C. 4-Hydroxybenzoic acid (974 g, 6.98 mol) and 2-phenoxyethyl bromide (1302 g, 6.34 mol) were added. Phosphorus tribromide (2.72 kg, 9.83 mol) was added via an addition funnel over a period of 2.5 hours at a rate as to keep temperature below 50° C. Stirring at 40-50° C. was continued for 1 hour and overnight (16 hours) without heating. Completion of the reaction was confirmed by NMR.

The reaction mixture was poured into a well stirred ice-water mixture (ca. 38 L) in a 50-L reactor. The resulting suspension was stirred for 2 hours. The aqueous phase was separated from the sticky solid on the bottom of the reactor and discarded after neutralization to pH 5. The sticky residue was washed with water (6 L) and then dissolved in ethyl acetate (32 L). The resulting organic solution was washed with 20% aqueous NaOH solution (3.2 L). The formed solid was separated by filtration, washed with ethyl acetate and discarded. The aqueous phase was separated from the organic filtrate and discarded. The combined ethyl acetate extract was washed with 10% NaHCO$_3$ solution (3 L), brine (5 L), then dried over MgSO$_4$ (1.5 kg). The solid of MgSO$_4$ hydrate was separated by filtration. The filtrate was dried over molecular sieves (1 kg), filtered, and evaporated in vacuo to an orange solid. The solid was washed with methyl t-butyl ether (2 L) and dried in vacuo at 40° C. over phosphorus pentoxide to constant weight to give the product in a yield of 1783.2 g (5.385 mol, 85%). HPLC purity of this material was determined to be 97%. $^1$H NMR (300 MHz, methanol-d4) 3.71-3.76 (2H, m, CH$_2$—Br), 4.37-4.42 (2H, m, CH$_2$—O), 6.86-6.90 (2H, m, Ar), 7.02-7.06 (2H, m, Ar), 7.65-7.75 (4H, m, Ar); $^{13}$C NMR (75 MHz, methanol-d4) 30.4, 69.6, 115.3, 116.1, 130.3, 132.4, 133.3, 133.7, 163.1, 163.3, 196.7.

The total combined amount of (4-(2-bromoethoxy)phenyl)(4-hydroxyphenyl)methanone prepared in this experiment and three other equal size runs was 8439 g (26.3 mol, averaged yield 82% as calculated from 2-phenoxyethyl bromide).

Example 3. Synthesis of 4-(1-(4-(2-bromoethoxy) phenyl)-2-phenylbut-1-enyl)phenol (3)

Zn dust (4.3 kg, 65.8 mol) was suspended in anhydrous dimethoxyethane (26 L) in a 100-L jacketed glass reactor under argon atmosphere, and the contents of the reactor were cooled to 2° C. Titanium tetrachloride (6 kg, 31.6 mol) was added at such a rate as to keep the temperature inside the reactor below 25° C. The mixture was heated to reflux and stirred for 1 hour, then left overnight at ambient temperature (15° C.). The reactor was then cooled to 5° C., and a solution of propiophenone (542 g, 4 mol) and (4-(2-bromoethoxy) phenyl)(4-hydroxyphenyl)methanone (1324 g, 4 mol) in anhydrous dimethoxyethane (10 L) was added to the reaction flask in one portion. The mixture was stirred and heated at reflux for 6 hours, then cooled to 60° C. and left overnight at ambient temperature. The content of the reactor was cooled to −3° C., and methyl t-butyl ether (30 L) was added. A 5% aqueous HCl solution (~13 L) was added via an addition funnel, and the mixture was stirred for 2 hours before the organic phase was separated. The remaining suspension was then passed through a Celite pad in order to separate the remaining excess of Zn powder. The aqueous filtrate was returned into the reactor and extracted thrice with methyl t-butyl ether (3×8 L), and the combined organic extracts were washed with brine (3×8 L) and dried over MgSO$_4$ (2 kg). Separation of MgSO$_4$ and removal of solvents in vacuo gave a brown oily residue (1703 g, 104%).

The oil was purified in two portions by column chromatography on silica gel eluted with methylene chloride. The first portion (935 g) of the crude bromide was eluted with methylene chloride through a column of 13" (diameter) and 18" (height) packed with 11.4 kg of silica gel. Collected fractions were analyzed by TLC and HPLC. Fractions of a suitable purity were combined and the solvent was removed in vacuo to give a white solid (641 g of a Z/E mixture with a purity of 98%, calculated as sum of E+Z isomers). The solid was combined with n-heptane (1.5 L) and the suspension was stirred for 1 h at 45° C. and then at ambient temperature for 16 hours. The solid was separated by filtration, and after drying in vacuo for 72 hours at ambient temperature, 644 g of 4-(1-(4-(2-bromoethoxy)phenyl)-2-phenylbut-1-enyl)phenol was obtained.

$^1$H NMR (300 MHz, CDCl$_3$) 0.91 (2×3H, t, CH$_3$—CH2), 2.40-2.50 (2×2H, 2q, C=C—CH$_2$—CH3), 3.53 (2H, t, CH$_2$—CH$_2$—Br), 3.64 (2H, t, CH$_2$—CH$_2$—Br), 4.14 (2H, t, CH$_2$—CH$_2$—O), 4.29 (2H, t, CH$_2$—CH$_2$—O), 4.6 (2×H, broad, Ar—OH), 6.45-6.49 (2H, m, Ar), 6.52-6.56 (2H, m, Ar), 6.69-6.90 (8H, m, Ar), 7.08-7.25 (14H, m, Ar); $^{13}$C NMR (75 MHz, CDCl$_3$) 156.6, 155.8, 154.1, 153.2, 142.4, 141.2, 137.4, 136.9, 136.4, 136.2, 135.8, 132.0, 131.9, 130.7, 130.6, 129.6, 127.7, 125.9, 114.9, 114.2, 113.5, 67.9, 67.6, 29.3, 29.2, 29.1, 13.7.

Example 4. Synthesis of a Mixture of E- and Z-Endoxifen

A jacketed glass reactor (100-L size) was charged with first ~55 L methylamine solution (33% solution in ethanol) and then 4-(1-(4-(2-bromoethoxy)phenyl)-2-phenylbut-1-enyl)phenol (1875 g, 4.429 mol). The reaction mixture was heated to 33° C. for 21 hours, at which point a TLC test indicated complete consumption of the starting bromide.

The solvent was removed in a 20-L rotary evaporator to give 3235 g of solid material. The solid was dissolved in dichloromethane (30 L) and the resultant solution was washed with a mixture of NaHCO$_3$ (2.6 kg) and Na$_2$CO$_3$ (1.4 kg) in water (32 L).

The aqueous phase was re-extracted once with dichloromethane (15 L), and the combined organic solution was dried over Na$_2$SO$_4$ (1.6 kg), filtered and concentrated in a 20-L evaporator to a tan solid. Acetone was added to the solid then removed in vacuo twice (7 L and 3 L of acetone, respectively) to give a solid (2164 g). The solid was dissolved in 5.9 L of acetone and the solution was heated to 65° C., and the resulting clear solution was slowly cooled to 20° C. for 19 hours and then kept in refrigerator at −10° C. for 4 days. The resulting crystalline material was collected by filtration (initial weight 2336 g) and dried in vacuo to give 1395 g of a mixture of E- and Z-Endoxifen. The filtrate was concentrated to provide an oily residue (314 g) which was dissolved in 950 mL of boiling acetone and then stored for 4 weeks at −10° C. The resultant crystalline material (100 g) was collected by filtration and dried in vacuo to a constant weight (73 g). Filtrate of the second crop, containing mostly impurities and E-isomer, was discarded. The total yield of endoxifen (E/Z-isomer ratio: 51/47) from two recrystallizations was 1468 g (87%).

$^1$H NMR (300 MHz, DMSO-d6) 0.85 (2×3H, t, CH$_3$—C), 2.28-2.34 (2×3H, 2s, CH$_3$—N), 2.3-2.5 (2×2H, m, C=C—CH$_2$), 2.73-2.82 (2×2H, 2t, CH$_2$—N), 3.85-4.02 (2×2H, 2t, CH$_2$—O), 6.4 (1H, d, Ar), 6.56-6.61 (4H, m, Ar), 6.65-6.80 (4H, m, Ar), 6.89-6.99 (4H, m, Ar), 7.05-7.20 (14H, m, Ar).

Example 5. Recrystallization of an Approximately 50/50 Mixture of Z and E Endoxifen Endoxifen (5512 g, E/Z ratio: ~50/50) was dissolved in 55 L of hot isopropyl acetate at 88° C. The clear solution was slowly cooled to 23° C. and kept for 6 hours. The crystalline material was collected in a filter funnel, washed with isopropyl acetate and dried in vacuo to a constant weight to give 2722 g (49%) of a material with an E/Z ratio of 68/30. The filtrate was concentrated to give a solid which was dried in vacuo to a constant weight to produce 2666 g (48%) of material enriched with the Z-isomer (E/Z-ratio: 19/77).

Example 6. Isomerization of an Endoxifen Mixture Enriched in E Isomer and Recrystallization to Produce Endoxifen Mixture Enriched in Z Isomer Endoxifen (2721 g, E/Z ratio ~70/30,) was suspended in isopropyl acetate (27 L) in a 100-L reactor. The suspension was heated at 85° C. for 2 hours. The E/Z ratio of the solution was determined to be ~1/1 by HPLC analysis. The mixture was cooled slowly to 15° C., resulting in the preferential crystallization of the E-isomer. The mother liquor (containing 71% Z-isomer) was removed from the reactor, evaporated to provide a solid and dried at 35° C. to constant weight: 1314 g (48%, Z-isomer content: 73%).

The above operations were repeated twice with the residual E-isomer crystals in the reactor to provide two additional crops of Z-enriched material: 817 g (Z-isomer content: 71%) and 220 g (Z-isomer content: 69%). The total amount of Z-enriched endoxifen isolated in this manner was 2348 gram (86%).

The residual crystalline material (342 g, 13%), collected from third recrystallization, was mainly (E)-Endoxifen with an isomeric purity of 96%. The material recovery of this step is 99%.

Example 7. Recrystallization of an Endoxifen Mixture Enriched in Z Isomer

Endoxifen (5013 g, E/Z ratio ~30/70) was dissolved in 50 L of acetone which was heated to reflux in a 100-L reactor. The resulting solution was cooled and stirred for 40 hours at 1 to 5° C. The mother liquor was removed from the reactor by aspiration. The remaining crystalline material was re-dissolved in boiling acetone (52 L). The resultant solution was stirred for 50 hours at 1 to 5° C. The mother liquor was removed. The remaining crystalline material was again dissolved in boiling acetone (48 L). The hot solution was filtered and kept for 22 hours at 1 to 5° C. The crystalline material which precipitated was collected by filtration and washed with ice-cooled acetone. The solid was dried in vacuo at 35° C. to a constant weight to give 1698 g (34%) of (Z)-endoxifen, with an isomeric purity of 99% (HPLC analysis). $^1$H NMR (300 MHz, DMSO-d6) 0.85 (3H, t, $CH_3$), 2.28 (3H, s, $CH_3$—N), 2.43 (2H, q, C=C—$CH_2$), 2.73 (2H, t, $CH_2$—N), 3.86 (2H, t, $CH_2$—O), 6.58 (2H, d, Ar), 6.69-6.77 (4H, m, Ar), 6.98 (2H, d, Ar), 7.10-7.18 (5H, m, Ar), 9.45 (1H, s, Ar—O—H); $^{13}$C NMR (100 MHz, DMSO-d6) 13.3, 28.5, 36.1, 50.3, 67.0, 113.3, 115.0, 125.9, 127.8, 129.3, 130.0, 131.3, 133.9, 135.5, 137.9, 139.9, 142.2, 156.1, 156.5; MS (ES-MS) 374.1 (MH+), 396.6 (M-Na+).

All portions of mother liquor were combined, concentrated in a 20-L evaporator to a solid and dried to a constant weight (2987 gram, 60%, E/Z 37/61). The overall recovery of material of this step is 94%.

What is claimed is:

1. A process for preparing (Z)-endoxifen, comprising
   (i) recrystallizing an input crystalline solid comprising a mixture of (Z)-endoxifen (1) and (E)-endoxifen (2) from a first solvent to provide a first crystalline solid and a first mother liquor, wherein the first mother liquor has a ratio of (1) to (2) at least 1.3 times greater than the ratio in the input crystalline solid;

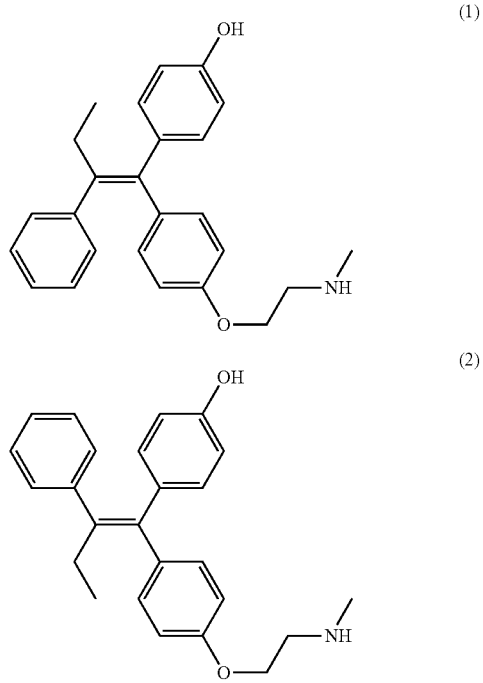

(ii) recrystallizing a solid produced by concentrating the first mother liquor, or by removal of the first solvent from the first mother liquor, from a second solvent to give a second crystalline solid and a second mother liquor;
   (iii) optionally recrystallizing the second crystalline solid from the second solvent one to five additional times to give a third crystalline solid;
   wherein the third crystalline solid has a ratio of (Z)-endoxifen (1) to (E)-endoxifen (2) greater than 20:1; wherein the first solvent is isopropyl acetate, toluene, methyl ethyl ketone, or methyl isobutyl ketone and the second solvent is methanol, ethanol, or acetone.

2. The process of claim 1, additionally comprising generating the input crystalline solid by reacting 4-(1-(4-(2-haloethoxy)phenyl)-2-phenylbut-1-enyl)phenol (3) with methylamine to produce a mixture of (Z)-endoxifen (1) and (E)-endoxifen (2), wherein X is chloro, bromo, or iodo

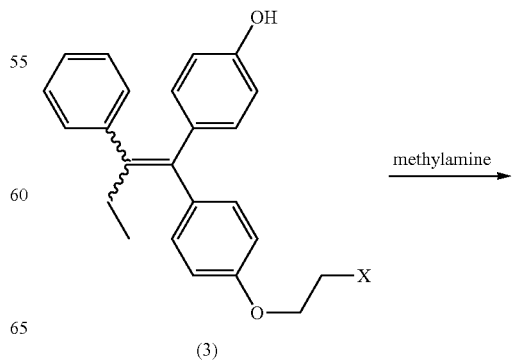

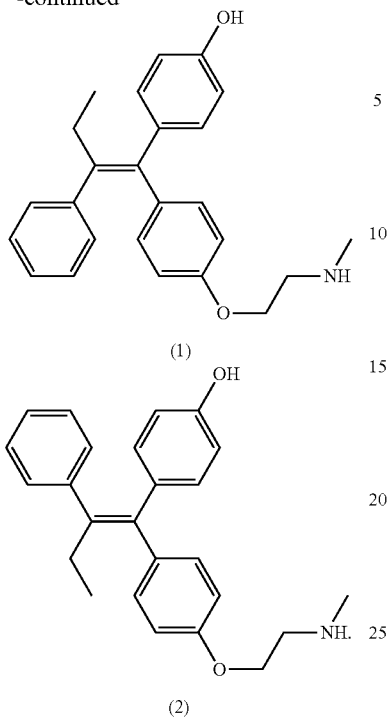

3. The process of claim 2, additionally comprising generating the 4-(1-(4-(2-haloethoxy)phenyl)-2-phenyl-but-1-enyl)phenol (3) by reacting a propiophenone (4) with (4-(2-haloethoxy)phenyl)(4-hydroxyphenyl) methanone (5) in the presence of a titanium halide reagent

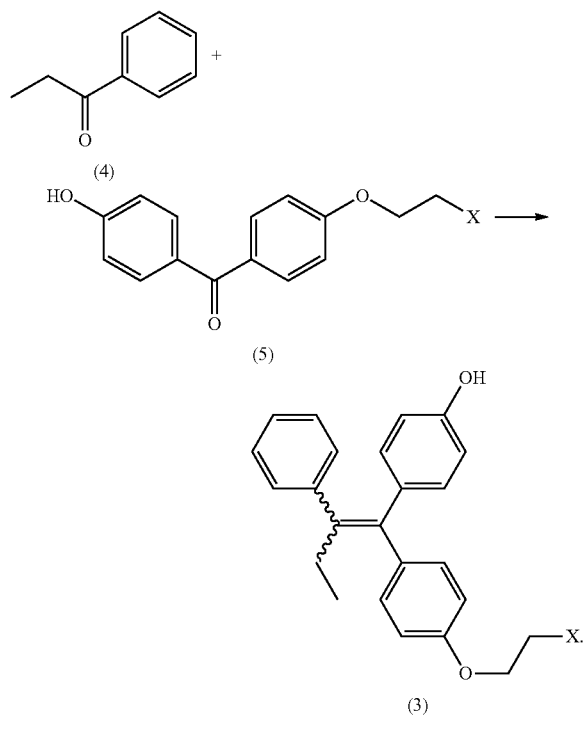

4. The process of claim 3, additionally comprising generating the (4-(2-haloethoxy)phenyl)(4-hydroxyphenyl)methanone (5) by reacting 4-hydroxybenzoic acid (6) with 1-(2-haloethoxy)benzene

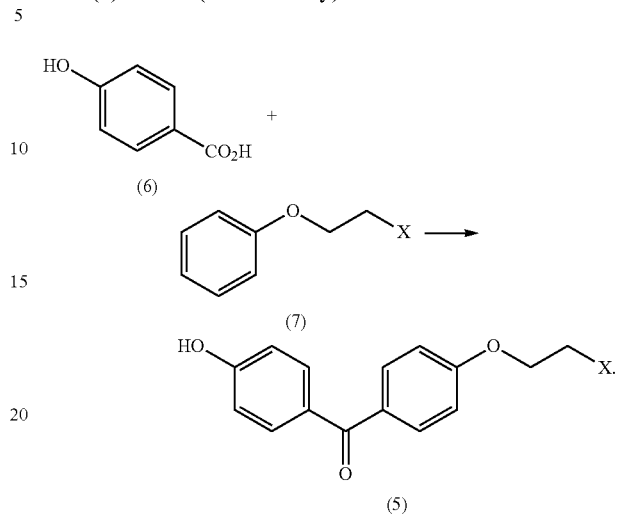

5. The process of claim 1, wherein the first solvent is isopropyl acetate and the second solvent is acetone.

6. The process of claim 1, wherein the third crystalline solid has a ratio of (Z)-endoxifen (1) to (E)-endoxifen (2) of 50:1 or greater.

7. The process of claim 1, wherein each recrystallization requires dissolving a compound or compounds to be recrystallized in solvent that is at a first temperature, and then cooling the resulting solution to a second temperature 20 to 100° C. lower than the first temperature.

8. The process of claim 2 wherein X is bromo.

9. The process of claim 1, wherein the recrystallizing of the second crystalline solid in step (ii) is performed 2 times to obtain the third crystalline solid.

10. The process of claim 2, wherein the reacting of 4-(1-(4-(2-haloethoxy)phenyl)-2-phenylbut-1-enyl)phenol (3) with methylamine occurs in methanol solvent.

11. The process of claim 3, wherein reacting propiophenone (4) with (4-(2-haloethoxy)phenyl)(4-hydroxyphenyl) methanone (5) is performed in the presence of zinc, and wherein the titanium halide reagent is titanium tetrachloride.

12. The process of claim 4, wherein the reacting of 4-hydroxybenzoic acid (6) with 1-(2-haloethoxy)benzene occurs in the presence of zinc bromide, polyphosphoric acid, and phosphorus tribromide.

13. The process of claim 1, further comprising
(iv) isomerizing a crystalline solid or mother liquor formed according to claim 1 wherein the ratio of (Z)-endoxifen (1) to (E)-endoxifen (2) is less than 0.9 to 1, by dissolving the crystalline solid or mother liquor in a third solvent and heating to between 60 and 100° C. for 0.5 to 4 hours, to produce an isomerized solution with a ratio of (Z)-endoxifen (1) to (E)-endoxifen (2) of approximately 1:1.

14. The process of claim 13, further comprising concentrating the isomerized solution to form an isomerized crystalline solid, and using the isomerized crystalline solid as the input crystalline solid for steps (i) through (iii).

15. The process of claim 13, further comprising
(v) cooling the isomerized solution by 30 to 100° C. to form a fourth crystalline solid and a fourth mother liquor, and removing the mother liquor followed by resubjecting the fourth crystalline solid to steps (iv) and (v) at least two times, and combining the resulting mother liquors to provide a combined mother liquor with a ratio of (Z)-endoxifen (1) to (E)-endoxifen (2) of at least 1.5 to 1.

16. The process of claim 15, further comprising designating the combined mother liquor as a first mother liquor and subjecting it to the same steps used for a first mother liquor.

17. A process for preparing (Z)-endoxifen, comprising (i) recrystallizing an input crystalline solid comprising a mixture of (Z)-endoxifen (1) and (E)-endoxifen (2) from isopropyl acetate to provide a first crystalline solid and a first mother liquor, wherein the first mother liquor has a ratio of (1) to (2) at least 1.3 times greater than the ratio in the input crystalline solid;

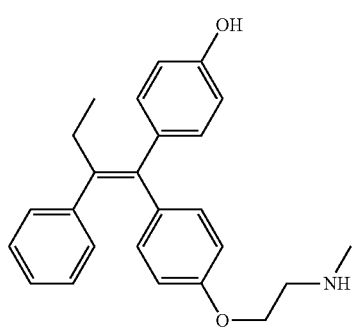

(1)

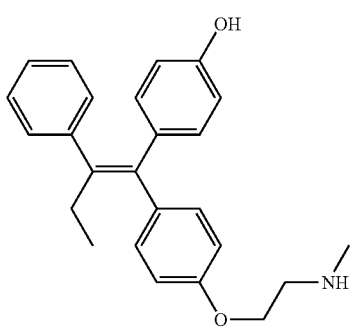

(2)

(ii) recrystallizing a solid produced by concentrating the first mother liquor, or by removal of the first solvent from the first mother liquor, from acetone to give a second crystalline solid and a second mother liquor;

(iii) optionally recrystallizing the second crystalline solid from acetone one to five additional times to give a third crystalline solid;

wherein the third crystalline solid has a ratio of (Z)-endoxifen (1) to (E)-endoxifen (2) greater than 50:1.

18. A process for preparing (Z)-endoxifen, comprising (i) dissolving a mixture of (Z)-endoxifen (1) and (E)-endoxifen (2) in isopropyl acetate, wherein the mixture contains has a ratio of (1) to (2) that is less than 1:1;

(ii) heating the mixture of (1) and (2) in isopropyl acetate at a temperature of 55° C. to 88° C. to obtain a second mixture of (1) and (2) having a ratio of (1) to (2) of about 1:1; and (iii) cooling the mixture to form a crystalline solid and a first mother liquor;

(iv) removing the first mother liquor from the crystalline solid; and (v) evaporating the first mother liquor to form a solid having a ratio of (1) to (2) that is greater than 1:1.

* * * * *